United States Patent [19]

Savarese et al.

[11] 4,235,906
[45] Nov. 25, 1980

[54] BIS-ISOQUINOLINIUM COMPOSITIONS AND METHODS OF USE

[75] Inventors: John J. Savarese, Boxford; Richard J. Kitz, Dover, both of Mass.; Sara Ginsburg, New York, N.Y.

[73] Assignee: Massachusetts General Hospital, Boston, Mass.

[21] Appl. No.: 7,952

[22] Filed: Jan. 31, 1979

Related U.S. Application Data

[63] Continuation-in-part of Ser. No. 926,794, Jul. 21, 1978, abandoned.

[51] Int. Cl.³ .................. A61K 31/47; C07D 217/10; C07D 217/20
[52] U.S. Cl. ................................. 424/258; 542/427; 546/140; 546/149
[58] Field of Search ................. 542/427; 424/258

[56] References Cited

U.S. PATENT DOCUMENTS

| | | | |
|---|---|---|---|
| 2,662,083 | 12/1953 | Eastland | 546/149 |
| 3,004,031 | 10/1961 | Taylor | 260/286 |
| 3,491,099 | 1/1980 | Copp | 546/149 |

FOREIGN PATENT DOCUMENTS

| | | |
|---|---|---|
| 2655883 | 6/1977 | Fed. Rep. of Germany . |
| 863717 | 3/1961 | United Kingdom . |
| 2002758 | 2/1979 | United Kingdom . |

OTHER PUBLICATIONS

Beilstein's Handbook of Org. Chem., vol. 9, 4th Ed., 1926, pp. 874, 875, 914.
Beilstein's Handbook of Org. Chem., vol. 9, 4th Ed., 3rd Suppl., 1971, pp. 4435, 4436, 4438.
"Chemical Abstracts," vol. 76 to 85, 1972-1976, p. 5886.
Gladych et al., Chem. Abstr., 57:3411i-3413f, (1962).
Kitz et al., "Biochem. Pharm.," vol. 18, pp. 871-881, (1969).
Danilov et al., "Br. J. Pharmac.," vol. 44, pp. 765-778, (1972).
Savarese et al., "Acta Anaesth. Scand.," Suppl. 53, pp. 43-58, (1973).
Savarese et al., "Anesthesia & Analgesia.," Current Res., vol. 52, No. 6, pp. 982-988, (1973).
Savarese et al., "Anesthesia & Analgesia.," Current Res., vol. 54, No. 5, pp. 669-678, (1978).
Brittain et al., "Brit. J. Pharm.," vol. 17, pp. 116-123, (1961).

*Primary Examiner*—Donald G. Daus
*Assistant Examiner*—Lisa Jones

*Attorney, Agent, or Firm*—Donald Brown

[57] ABSTRACT

Intermediate-duration reversible neuromuscular blocking agents of the formula (I)

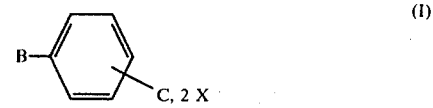

where B and C are preferably para or may be meta and are each

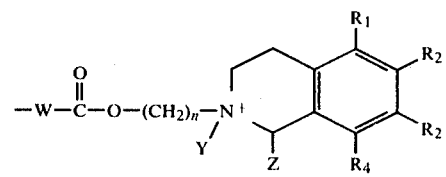

where W is $CH_2$ or most preferably $CH\!=\!CH$ $R_1$, $R_2$, $R_3$ and $R_4$ are the same or different and are each hydrogen or lower alkoxy of 1 to 4 carbon atoms and preferably methoxy, Y is lower alkyl of 1 to 4 carbon atoms and preferably methyl, % is hydrogen, lower alkyl of 1 to 4 carbon atoms, cyclopentyl, cyclohexyl, benzyl, or

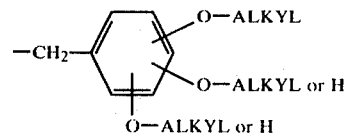

where ALKYL has 1 to 4 carbon atoms preferably where the O-ALKYL is at the 2, 3, 4 or 5 positions such as 4-methoxy benzyl and is most preferably 3,4-dimethoxy benzyl or 3, 4, 5-trimethoxybenzyl, n is 2, 3 or 4, most preferably 2 or 3 provided that at least one of $R_1$ to $R_4$ is lower alkoxy and most preferably where $R_1$ and $R_4$ is hydrogen and $R_2$ and $R_3$ are methoxy and X is a pharmaceutically acceptable anion.

The neuromuscular blocking agents of formula I are useful for administration to a patient to cause skeletal muscle relaxation during surgery and are normally administered intravenously in a pharmaceutically acceptable carrier.

97 Claims, No Drawings

BIS-ISOQUINOLINIUM COMPOUNDS, COMPOSITIONS AND METHODS OF USE

PRIOR APPLICATION

This application is a continuation-in-part of U.S. Pat. application Ser. No. 926,794 filed July 21, 1978, now abandoned.

BACKGROUND OF THE DISCLOSURE

In anesthesia, neuromuscular blocking agents are used to provide skeletal muscular relaxation during surgery and during intubation of the trachea. In general there are two types of neuromuscular blocking agents in use, nondepolarizing and depolarizing. The nondepolarizing agents include d-tubocurarine, pancuronuim gallamine, diallyltoxiferine, and toxiferine.

The depolarizing agents include succinylcholine and decamethonium. All of the conventional nondepolarizing agents when used for producing skeletal muscle relaxation in surgery have a long duration of action e.g., 60 to 180 minutes in man. The depolarizing agents on the other hand provide muscle relaxation at dosages normally used for surgery which is less than the duration of action of nondepolarizing agents.

For example, succinylcholine provides a short duration of action of about 5 to 15 minutes whereas decamethonium provides about 20 to 40 minutes duration of muscle relaxation. To the best of applicants' knowledge there are no nondepolarizing agents currently available for approved clinical use which have an intermediate duration of action. As used herein, an intermediate duration of action is defined as about 15 to 30 minutes in cats and monkeys.

The long duration of action of nondepolarizing agents is unacceptable in many surgical procedures which take less than one hour because the patient is not generally fully recovered from their effects e.g., the patient may be unable to breathe adequately on his or her own.

Each nondepolarizing agent has inherent side-effects. For example, gallamine and pancuronium may cause tachycardia, and d-tubocurarine and diallyltoxiferine may cause hypotension. While such drugs can be pharmacologically antagonized with anticholinesterase agents, this obviously necessitates the administration of a second drug which itself may have its own side effects e.g., bradycardia, gut spasm and bronchorrhea. Thus to overcome the aforementioned side-effects of the anticholinesterase agents, a third drug, an anticholinergic drug e.g., atropine must also be given.

The depolarizing agents to the best of applicants' knowledge have no pharmacological antagonists. While in most cases there is no need to reverse the effects of the depolarizing agents, in certain patients the effects are much prolonged because of abnormal metabolism of the agent by the patient.

The polarizing agents due to the mode of action which initially causes skeletal muscle contraction and stimulation of smooth muscles are also known to cause the following side-effects in certain instances; increased intraocular, and intragastric tension, cardiac arrhythmias, potassium release, and muscle pain. These side-effects caused by the depolarizing agents are not caused by the nondepolarizing agents. It is therefore clearly evident that a new neuromuscular blocking agent having the relatively few side-effects and the reversibility of the nondepolarizing agents yet being of considerably shorter i.e., intermediate, duration of action is needed. No such drug is in clinical use at the present time.

It should be understood that while nondepolarizing agents generally have few side-effects, gallamine and pancuronium may cause tachycardia and d-tubocurarine and diallyltoxiferine may cause hypotension. Surprisingly, the compounds of the present invention also appear to be free of these side-effects at the dosages anticipated being used clinically in tests made to date. Reference may be had to the text of: "The Pharmacological Basis of Therapeutics"—Fifth Edition, edited by Louis S. Goodman and Alfred Gilman published by the The McMillian Co., Copyright 1975, Chapter 28, author George B. Koelle, for a further description of neuromuscular blocking agents.

Reference should also be had to the following articles: "Neuromuscular Blocking Activity of a New Series of Quaternary N-Substituted Choline Esters"—British Journal of Pharmacology, September 1971, vol. 43, No. 1, p. 107.

"The Pharmacology of New Short Acting Nondepolarizing Ester Neuromuscular Blocking Agents: Clinical Implications"—published in Anesthesia and Analgesia... Current Researches, Vol. 52, No. 6, p. 982 Nov.-Dec., 1973;

"Potential Clinical Uses of Short-Acting Nondepolarizing Neuromuscular-Blocking Agents as Predicted from Animal Experiments"—published in Anesthesia and Analgesia... Current Researches, Vol. 54, No. 5, Sept.-Oct., 1974;

"U.S. Pat. No. 3,491,099" for a further description of neuromuscular blocking agents; and "Does Clinical Anesthesia Need New Neuromuscular Blocking Agents?"—published in Anesthesiology, Vol. 42, No. 3, March 1975, P. 236.

BRIEF DESCRIPTION OF THE DISCLOSURE

The present invention provides new and improved neuromuscular blocking agents sometimes called muscle relaxants which combine a nondepolarizing mode of action with the intermediate duration of action and reversibility needed to meet improved clinical requirements for use during surgery.

The intermediate-duration reversible neuromuscular blocking agents of the formula (I)

$$B-\underset{}{\bigcirc}-C \cdot 2X^- \quad (I)$$

where B and C are preferably para or may be meta and are each $$-W-\overset{O}{\underset{\|}{C}}-O-(CH_2)_n-\underset{Y}{N^+}\diagdown\underset{Z}{\overset{R_1}{\underset{R_4}{\bigcirc}}}\overset{R_2}{\underset{R_2}{}}$$

where W is $CH_2$ or $CH=CH$
$R_1$, $R_2$, $R_3$ and $R_4$ are the same or different and are each hydrogen or lower alkoxy of 1 to 4 carbon atoms and preferably methoxy, Y is lower alkyl of 1 to 4 carbon atoms and preferably methyl, Z is hydrogen, lower alkyl of 1 to 4 carbon atoms, cyclopentyl, cyclohexyl, benzyl, or

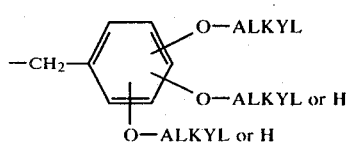

where ALKYL has 1 to 4 carbon atoms preferably where the O ALKYL is at the 2, 3, 4, or 5 positions such as 4-methoxy benzyl and is most preferably 3, 4-dimethoxy benzyl or 3, 4, 5-trimethoxybenzyl, n is 2, 3 or 4, most preferably 2 or 3 provided that at least one of $R_1$ to $R_4$ is lower alkoxy and most preferably where $R_1$ and $R_4$ is hydrogen and $R_2$ and $R_3$ are methoxy and X is a pharmaceutically acceptable anion.

In the above alkyl of 1 to 4 carbon atoms is meant to include branched or straight chain alkyl (e.g., methyl, ethyl, propyl, butyl, etc.,) and alkoxy of 1 to 4 carbon atoms is meant to include methoxy, ethoxy, propoxy and butoxy. Of the compounds of the invention the most preferred are the compounds of the formula II

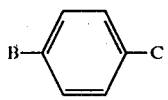

(II)

where B and C are as defined above, where
W is $CH_2$ or $CH=CH$
n is 3, Y is methyl and Z is 3,4-dimethoxy benzyl or 3, 4, 5-trimethoxy benzyl, $R_1$ and $R_4$ are hydrogen and $R_2$ and $R_3$ are methoxy.

Of the compounds of special note there is mentioned the following with the substitutions as set forth below based on the structure of formula II and identified as follows:

(KK-100) n is 3, Y is methyl, W is $CH_2$, $R_1$ and $R_4$ are hydrogen, $R_2$ and $R_3$ are methoxy and Z is 3, 4-dimethoxybenzyl;

(LL46) n is 3, Y is methyl, W is $CH_2$, $R_1$ and $R_4$ are hydrogen, $R_2$ and $R_3$ are methoxy and Z is 3, 4, 5-trimethoxybenzyl; p (HH109) n is 3, Y is methyl, W is $CH=CH$, $R_1$ and $R_4$ are hydrogen, $R_2$ and $R_3$ are methoxy and Z is 3, 4, 5-trimethoxybenzyl where B is para to C and (LL39) where the substituents are the same as in (HH109) and B is meta to C.

(GG195)n is 3, Y is methyl, W is $CH=CH$, $R_1$ and $R_4$ are hydrogen, $R_2$ and $R_3$ are methoxy and Z is 3, 4-dimethoxybenzyl.

The above specifically mentioned compounds are most preferred as intermediate duration compounds in that they have relatively low but still measurable hydrolysis rates which distinguishes them from short acting neuromuscular blocking agents. The compounds where W is $CH=CH$ are most preferred because of both their activity and few side effects and most particularly the compounds (HH109) and (LL39), are by far the best at this time since they exhibit fewest side-effects and very high potency.

Of the anions of the invention, the following are examples of those which are suitable: iodide, mesylate, tosylate, bromide, benzene sulfonate, nitrobenzene sulfonate, naphthylene sulfonate, chloride, sulfate, phosphate, hydrogen phosphate acetate and propionate. The mesylate and chloride cations are most preferred because of the solubility of the salt made therefrom in water. Since the activity is in the cation portion of the compound, the nature of the anion is unimportant as long as it is pharmaceutically acceptable.

The compounds of formula I or II are used as neurmuscular blocking agents in conjunction with surgery or for intubation of the trachea by conventional parenteral administration e.g., intramuscular or intravenous administration in solution. The compounds of the present invention shown in formulas I or II are administered to patients such as monkeys and man (humans) and other mammals to achieve a neuromuscular block. The dosage for each type of patient will vary because of the peculiarities of the species, however, a suitable intravenous amount or dosage of the compounds of formula I or II for a monkey would be 0.05 to 0.8 mg/kg of body weight, and for a man 0.05 to 0.8 mg/kg of body weight, and most preferably 0.1 to 0.5 mg/kg of body weight, the above being based on the weight of the cation which is the active ingredient.

The compounds of this invention would normally be readministered every 15 to 30 minutes after initial administration or given as a slow continuous infusion depending upon the length of time a muscular block is desired, and as determined by the anesthetist and surgeon in charge of the patient. The compounds of this invention are reversible using conventional anticholinesterase agents such as neostigmine and edrophonium and appear to avoid the side-effects associated with the depolarizing agents.

The compounds of formula I or II are therefore useful for producing an intermediate duration neuromuscular blockage, and the present invention provides a method of producing such blockage in mammals e.g., man or monkeys, by intravenously injecting a dose of 0.05 to 0.8 mg/kg to the mammal.

The compounds may be presented in a pharmaceutical formulation for parenteral administration. The formulation may be an aqueous on non-aqueous solution or emulsion in a pharmaceutically acceptable liquid or mixture of liquids, whch may contain bacteriostatic agents, antioxidants, buffers, thickening agents, suspending agents or other pharmaceutically acceptable additives.

Such formulations are normally presented in unit dosage forms such as ampoules or disposable injection devices, or in multidose forms such as a bottle from which the appropriate dose may be withdrawn. All such formulations should be rendered sterile.

The compounds of this invention may be presented as a powder e.g., as a unit dose in a sealed vial to which sterile water may be added by a needle, e.g., through a seal thereof (such as rubber). A suitable unit dose to obtain a neuromuscular block for mammals e.g., humans or monkeys is about 1 mg to 100 mg and most preferably 3 to 50 mg. Thus a suitable pharmaceutical parenteral preparation will preferably contain 20 to 100 mg of the compounds of formulas I or II of this invention in solution. A pharmaceutical formulation may conventional contain 5 to 400 mg, or 10 to 400 mg, and most preferably 5 to 200 mg. of the compounds of this invention. A simple and preferred formulation is a solution of the compound of formula I or II in water which may be prepared by simply dissolving the compound into previously sterilized pure, i. e., pyrogen free water under aseptic conditions and sterilizing the solution.

The compound of formula I or II may also be administered as an infusion of a dextrose solution or a saline solution e.g., Ringers' Solution. The compounds (formulas I or II) of this invention may be prepared by the following methods:

METHOD 1

Appropriately substituted tetrahydroisoquinolines are prepared in the customary fashion from appropriately substituted phenylethylamines and phenylactic acids by the Bischler-Napieralski reaction. The tertiary tetrahydroisoquinoline is quanternized with an appropriate α bromo ω chloro, α- Iodo ω chloro, or α-Iodo ω bromo alkane. The resulting N-alkyl-N-(ω-haloalkyl) tetrahydroisoquinolinium halide is boiled in water with the silver salt of the appropriate dicarboxylic acid, yielding silver halide and the benzylisoquinolinium salt of the acid. This salt rearranges to the corresponding ester on heating: for example, the general reaction using α-bromo ω-chloro alkane is illustrated as follows;

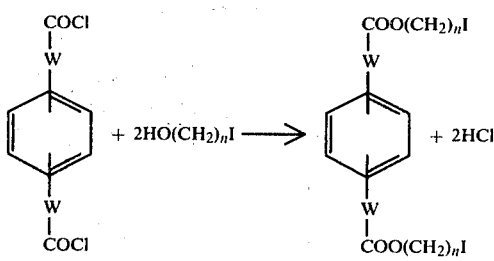

The diiodoester is refluxed with in excess of, two moles of an appropriate tetrahydroisoquinoline prepared in standard fashion by the Bischler-Napieralski reaction as described in Method I. The desired bis-tetrahydroisoquinolinium diiodide (disalt) is obtained.

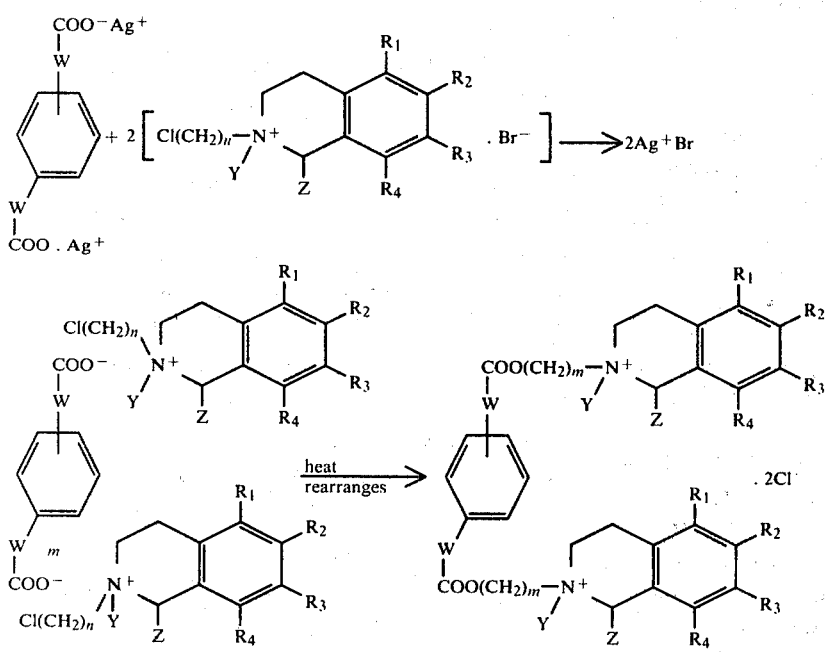

where $W = CH_2$ or $CH = CH$, and n, Y, % and $R_1$ to $R_4$ are as previously defined. Other salts are prepared by conventionally reacting the dichloro salt in an ion exchange reaction with an appropriate salt of the desired anion e.g., silver mesylate, silver tosylate, etc.

METHOD 2

The-bis-acid chloride of an appropriate phenylene dicarboxylic acid is prepared in the usual fashion by treatment of the acid with thionyl chloride. The acid chloride is esterified with an appropriate α-hydroxy-ω-iodoalkane, yielding the desired phenylene diacyl bis-ω-iodoalkyl ester:

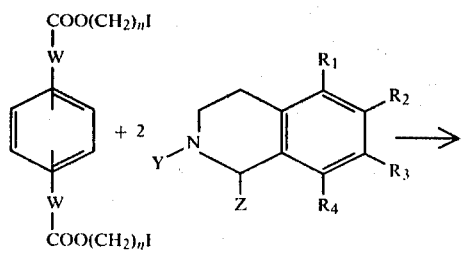

-continued

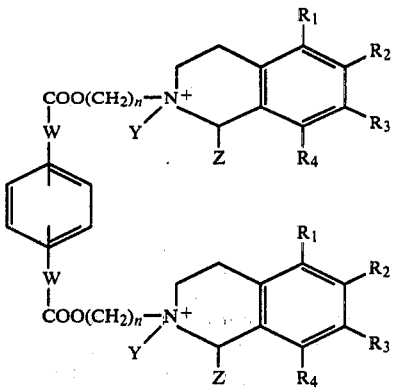

where ω is CH₂ or CH=CH and n, Y, %, and R₁ to R₄ are defined as above. The desired salts are then prepared in a conventional ion exchange reaction as described in Method I.

The following examples illustrate the invention. Temperatures are in degrees centigrade.

EXAMPLE 1

Preparation of Bis-3-[N-methyl-1-(3,4,5-trimethoxybenzyl)6,7-dimethoxy-1,2,3,4-tetrahydroisoquinolinium]propyl p-phenylene-3,3'-diacrylate dichloride (HH109)

1. Preparation of silver p-phenylene diacrylate

| | |
|---|---|
| p-phenylene diacrylate acid 4.4 gm = | 40 meq |
| H₂O | 60 ml |
| KOH 1N | 40 ml |

The mixture is heated to boiling, and, if necessary, the pH is adjusted to 7.0 with the same acid. AgNO₃ 6.8 gm=40 m M is added to the yellow hot solution. Immediately a heavy precipitate forms. The mixture is cooled and filtered and the filter cake is washed with water, refiltered and dried. Yield=quantitative. The product is an amorphous, slightly colored powder. It is pulverised for use in the next step.

2. Preparation of 5'-Methoxylaudanosine

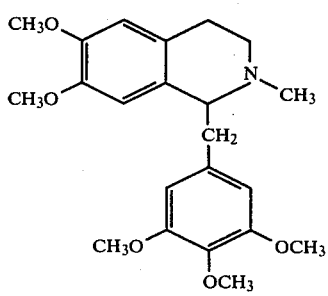

3,4-dimethoxyphenylethylamine and 3,4,5-trimethoxyphenylacetic acid are heated together at 165°–190° in a flask until bubbling of water subsides. The product, N-(3,4,5-trimethoxyphenyl acetyl) homoveratrylamine, is recrystallized from methanol Yield=80% m.p.=94°.

3.9 gm (10 mM) N-(3,4,5-trimethoxyphenylacetyl)-homoveratrylamine is refluxed in 15 ml toluene together with 5 ml POCl₃ for 2 hours. The settled semisolids are carefully separated (POCl₃ excess!) and the free base liberated by adding excess of NaOH and extracted with benzene. The product, 6,7-dimethoxy-1-(3',4',5'-trimethoxybenzyl)3,4-dihydroisoquinoline is refluxed in acetone or benzene with an excess of methyl iodide. The quaternary salt, 6,7-dimethoxy-1-(3', 4', 5'-trimethoxybenzyl)2-methyl, 3,4-dihydroisoquinolinium iodide, precipitates out. m.p.=224°.

5.1. gm (10 mM) 6,7-dimethoxy-1-(3',4', 5'-trimethoxybenzyl)2-methyl 3,4-dihydroisoquinolinium iodide is dissolved in 80 ml H₂O and 16 ml concentrated HCl. Zinc dust (1 1. gm) is added in small portions to the boiling stirred solution. The yellow color disappears (reaction time 15–20 minutes). The mixture is filtered hot from some unreacted zinc and rendered alkaline with concentrated NaOH. It is impractical to filter the partly precipitated zinc hydroxide, so to avoid emulsions, the whole mixture is carefully shaken with chloroform. The residue of the chloroform solution is redissolved in ether and the ether insolubles are filtered off. The ether residue does not crystallize on standing. This amine is a gummy material which hardens on standing. The crude amine is used for the next step.

3. Preparation of N-(3-chloropropyl)5'-methoxylaudanosinium bromide

5'-Methoxylaudanosine 1.4 gm=4 mM is dissolved in 8 ml. dimethylformamide by warming slightly. 1-bromo-3-chloropropane 1,2 gm (about 100% excess) is added and the mixture is left at room temperature for 5 days. (Sometimes part of the unreacted 5'-methoxylaudanosine crystallizes out, but eventually it redissolves).

The reddish-orange solution is treated with a large amount of ether and the precipitated gummy quaternary salt is decanted and slurried in fresh ether. After standing in ether for one day, low melting solids are obtained. Yield=1.6 gm, about 80% of theory.

4. Preparation of p-phenylene diacrylic diester of N-propyl-5'-methoxylaudanosine (HH109) (Horenstein - Pahlicke Ester Formation)

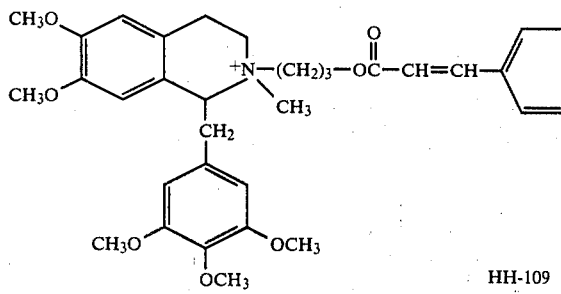
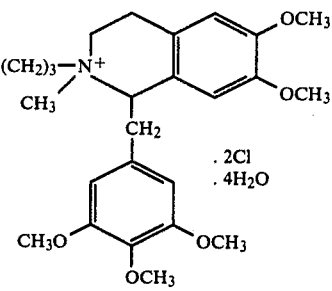

HH-109

N-(3-chloropropyl)5'-methoxylaudanosinium bromide 2.1 gm = 4 mH
Silver p-phenylene diacrylate 0.85 g = 4 meg
H₂O about 150 ml The mixture is boiled in an open beaker for about 10-15 minutes, stirring by hand from time to time. At the boiling temperature the silver salt is slightly soluble and reacts with the quaternary bromide. The mixture is cooled to room temperature, filtered straight and the aqueous solution is evaporated to dryness in a large dish on a steam bath. Continued heating of the residue is done for about 2 hours, after which rearrangement to the ester is complete.

The amorphous residue is boiled with isopropanol (about 40 ml) and filtered hot from some trace mechanical impurities. Gums precipitate from the filtrate at room temperature and the precipitation is completed at about −3° overnight. The supernatant is decanted and the material is slurried in ethyl acetate twice.

By now the gum is semisolid and can be filtered off. After careful drying at 75° the gums become solids. At this stage they still probably retain water in varying degrees. Yield=1.0 gm (about 40%). Yields vary from batch to batch.

EXAMPLE 2

Preparation of Bis-3-(N-methyl-1-(3,4,5-trimethoxybenzyl)6,7-dimethoxy-1,2,3,4-tetrahydroisoquinolinium]propyl p-phenylene-3,3'-diacetate dichloride (LL46)

1. Preparation of silver p-phenylene diacetate

| | |
|---|---|
| p-phenylene diacetic acid 4.4 gm = purchased from Aldrich | 40 meq, |
| H₂O | 60 ml |
| KOH 1N | 40 ml |

The mixture is heated to boiling, and, if necessary, the pH is adjusted to 7.0 with the same acid. AgNO₃ 6.8 gm=40 mM is added to the yellow hot solution. Immediately a heavy precipitate forms. The mixture is cooled and filtered and the filter cake is washed with water, refiltered and dried. Yield=quantitative. The product is an amorphous, slightly colored powder. It is pulverized for use in the next step.

2. Preparation of 5'-methoxylaudanosine

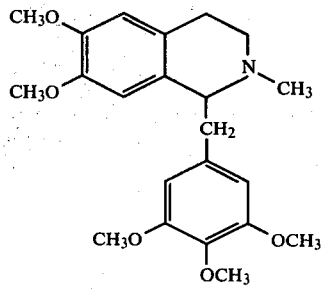

3,4-dimethoxyphenylethylamine and 3,4,5-trimethoxyphenylacetic acid are heated together at 165-190° in a flask until bubbling of water subsides. The product, N-(3,4,5-trimethyoxyphenylacetyl)homoveratrylamine, is recrystallized from methanol. Yield=80%. m.p.=94°.

3.9 gm (10 mM) N-(3,4,5-trimethoxyphenylacetyl)-homoveratrylamine is refluxed in 15 ml toluene together with 5 ml POCl₃ for 2 hours. The settled semisolids are carefully separated (POCl₃ excess!) and the free base liberated by adding excess of NaOH and extracted with benzene. The product, 6,7-dimethoxy-1-(3',4',5'-trimethoxybenzyl)3,4-dihydroisoquinoline is refluxed in acetone or benzene with an excess of methyl iodide. The quaternary salt, 6,7-dimethoxy-1-(3',4',5'-trimethoxybenzyl)2-methyl3,4-dihydroisoquinolinium iodide, precipitates out. m.p.=224°.

5.1 gm (10 mM) 6,7-dimethoxy-1-(3',4',5'-trimethoxybenzyl)2-methyl3,4-dihydroisoquinolinium iodide is dissolved in 80 ml H₂O and 16 ml concentrated HCl. Zinc dust (1.1 gm) is added in small portions to the boiling stirred solution. The yellow color disappears (reaction time 15-20 minutes). The mixture is filtered hot from some unreacted zinc and rendered alkaline with concentrated NaOH. It is impractical to filter the partly precipitated zinc hydroxide, so to avoid emulsions, the whole mixture is carefully shaken with chloroform. The residue of the chloroform solution is redissolved in ether and the ether insolubles are filtered off. The ether residue does not crystallize on standing. This amine is a gummy material which hardens on standing. The crude amine is used in the next step.

3. Preparation of N-(3-chloropropyl)5'-methoxylaudanosinium bromide

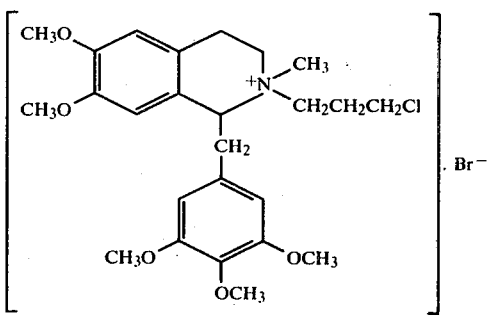

5′-Methoxylaudanoisine 1.4 gm=4 mM is dissolved in 8 ml dimethylformamide by warming slightly. 1-bromo-3-chloropropane 1.2 gm (about 100% excess) is added and the mixture is left at room temperature for 5 days. (Sometimes part of the unreacted laudanosine crystallizes out, but eventually it redissolves).

The reddish-orange solution is treated with a large amount of ether and the precipitated gummy quaternary salt is decanted and slurried in fresh ether. After standing in ether for one day, low melting solids are obtained. Yield=1.6 gm, about 80% of theory.

4. Preparation of p-phenylene diacetic-diester of N-propyl 5′methoxylaudanosine (LL46) (Horenstein - Pahlicke Ester formation)

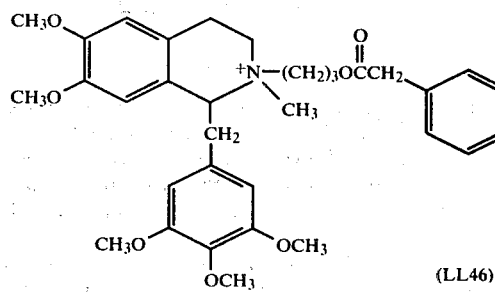

N-(3-chloropropyl)5′-methoxylaudanosinum bromide 2.1 gm = 4 mM
Silver p-phenylene diacetate 0.85 gm = 4 meg
H₂O about 150 ml The mixture is boiled in an open beaker for about 10–15 minutes, stirring by hand from time to time. At the boiling temperature the silver salt is slightly soluble and reacts with the quaternary bromide. The mixture is cooled to room temperature, filtered straight and the aqueous solution is evaporated to dryness in a large dish on a steam bath. Continued heating of the residue is done for about 2 hours, after which the rearrangement to the ester is complete.

The amorphous residue is boiled with isopropanol (about 10 ml) and filtered hot from some trace mechanical impurities gums precipitate from the filtrate at room temperature and the precipitation is completed at about −3° overnight. The supernatant is decanted and the material is slurried in ethyl acetate twice. By now the gum is semisolid and can be filtered off. After careful drying at 75° the gums become solids. At this stage they still probably retain water in varying degrees. Yield=1.0 gm (about 40%). Yields vary from batch to batch. M.P.=80°–90° (decomposes)

EXAMPLE 3

Preparation of Bis-3-[N-methyl-1-(3,4-dimethoxybenzyl)6,7-dimethoxy-1,2,3,4-tetrahydroisoquinolinium]propyl p-phenylene-3,3′-diacrylate dichloride. (GG195)

1. Preparation of silver p-phenylene diacrylate

| p-phenylene diacrylate acid 4.4 gm = purchased from Aldrich | 40 meq. |
|---|---|
| H₂O | 60 ml |
| KOH 1N | 40 ml |

The mixture is heated to boiling, and, if necessary, the pH is adjusted to 7.0 with the same acid. AgNO₃ 6.8 gm=40 mM is added to the yellow hot solution. Immediately a heavy precipitate forms. The mixture is cooled and filtered and the filter cake is washed with water, refiltered and dried. Yield=quanitative. The product is an amorphous, slightly colored powder. It is pulverized for use in the next step.

Preparation of 3-chloropropyl laudanosinium bromide:

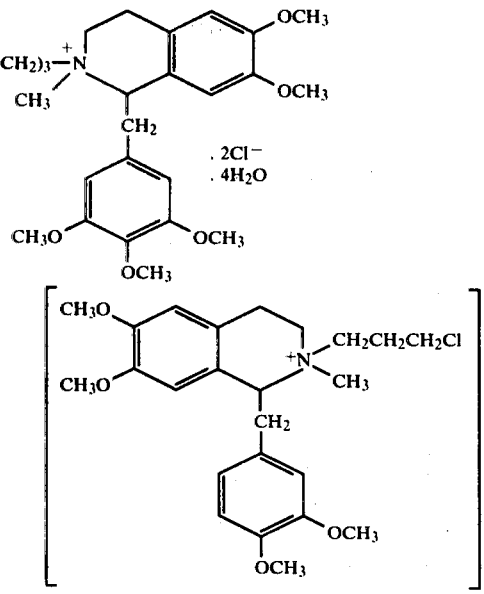

Laudanosine (Aldrich) 1.4 gm=4 mM is dissolved in 8 ml dimethylformamide by warming slightly. 1-bromo-3-chloropropane 1.2 gm (about 100% excess) is added and the mixture is left at room temperature for 5 days. (Sometimes part of the unreacted laudanosine crystallizes out, but eventually it redissolves).

The reddish-orange solution is treated with a large amount of ether and the precipitated gummy quaternary salt is decanted and slurried in fresh ether. After standing in ether for one day, low melting solids are obtained. Yield=1.6 gm, about 80% of theory.

3. Preparation of p-phenylene diacrylic diester of N-propyl laudanosine (GG195) (Horenstein - Pahlicke Ester Formation)

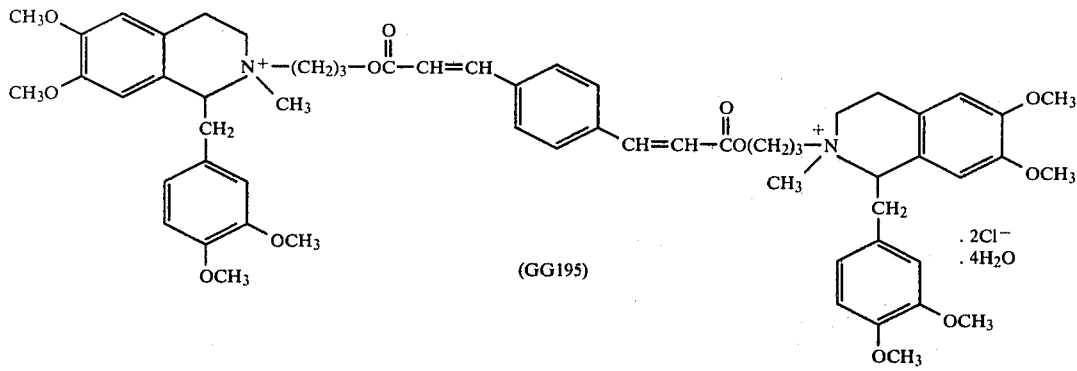
(GG195)

N-(3-chloropropyl) laudanosinium bromide 2.1 gm = 4mM
Silver p-phenylene diacrylate 0.85 gm = 4meq
H₂O about 150 ml The mixture is boiled in an open beaker for about 10-15 minutes, stirring by hand from time to time. At the boiling temperature the silver salt is slightly soluble and reacts with the quaternary bromide. The mixture is cooled to room temperature, filtered straight and the aqueous solution is evaporated to dryness in a large dish on a steam bath. Continued heating of the residue is done for about 2 hours, after which the rearrangement to the ester is complete.

The amorphous residue is boiled in isopropanol (about 40 ml) and filtered hot from some trace mechanical impurities. Gums precipitate from the filtrate at room temperature and the precipitation is completed at about −3° overnight. The supernatant is decanted and the material is slurried in ethyl acetate twice. By now the gum is semisolid and can be filtered off. After careful drying at 75° the gums becomes solids. At this stage they still probably retain water in varying degrees. Yield = 1.0 gm (about 40%). Yields vary from batch to batch.

EXAMPLE 4

Preparation of Bis-3-[N-methyl-1-(3,4-dimethoxybenzyl) 6,7-dimethoxy-1,2,3,4-tetrahydroisoquinolinium]propyl p-phenylene-3,3'-diacetate dichloride. (KK100).

1. Preparation of silver p-phenylene diacetate

| | |
|---|---|
| p-phenylene diacetic acid 4.4 gm = purchased from Aldrich | 40 meq, |
| H₂O | 60 ml |
| KOH 1N | 40 ml |

| | |
|---|---|
| p-phenylene diacetic acid 4.4 gm = purchased from Aldrich | 40 meq, |
| H₂O | 60 ml |
| KOH 1N | 40 ml |

The mixture is heated to boiling, and, if necessary, the pH is adjusted to 7.0 with the same acid. AgNO₃ 6.8 gm = 40 mM is added to the yellow hot solution. Immediately a heavy precipitate forms. The mixture is cooled and filtered and the filter cake is washed with water, refiltered and dried. Yield = quanitative. The product is an amorphous, slightly colored powder. It is pulverized for use in the next step.

2. Preparation of 3-chloropropyl laudanosinium bromide:

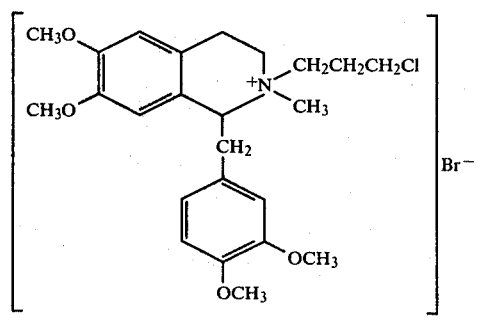

Laudanosine (Aldrich) 1.4 gm = 4 mM is dissolved in 8 ml dimethylformamide by warming slightly. 1-bromo-3-chloropropane 1.2 gm (about 100% excess) is added and the mixture is left at room temperature for 5 days. (Sometimes part of the unreacted laudanosine crystallizes out, but eventually it redissolves).

The reddish-orange solution is treated with a large amount of ether and the precipitated gummy quaternary salt is decanted and slurried in fresh ether. After standing in ether for one day, low melting solids are obtained. Yield = 1.6 gm, about 80% of theory.

3. Preparation of p-phenylene diacetic diester of N-propyl laudanosine (KK100) (Horenstein - Pahlicke Ester Formation)

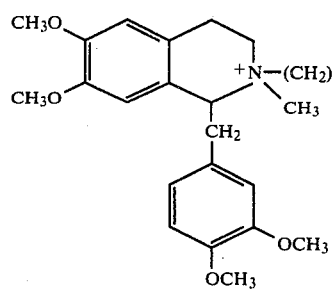 (KK100) 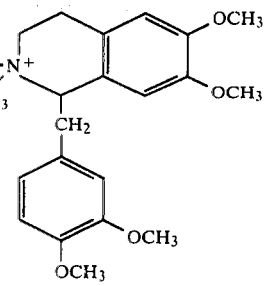

N-(3-chloropropyl) laudanosinium bromide 2.1 gm = 4 mM
Silver p-phenylene diacetate 0.85 gm = 4meq
H₂O about 150 ml The mixture is boiled in an open beaker for about 10–15 minutes, stirring by hand from time to time. At the boiling temperature the silver salt is slightly soluble and reacts with the quaternary bromide. The mixture is cooled to room temperature, filtered straight and the aqueous solution is evaporated to dryness in a large dish on a steam bath. Continued heating of the residue is done for about 2 hours, after which the rearrangement to the ester is complete:

The amorphous residue is boiled with isopropanol (about 40 ml) and filtered hot from some trace mechanical impurities. Gums precipitate from the filtrate at room temperature and the precipitation is completed at about −3° overnight. The supernatant is decanted and the material is slurried in ethyl acetate twice. By now the gum is semisolid and can be filtered off. After careful drying at 75° the gums become solids. At this stage they still probably retain water in varying degrees. Yield = 1.0 gm (about 40%). Yields vary from batch to batch. M.P. = 80°–90° (decomposes).

EXAMPLE 5

Pharmaceutical formulation (HH109) is dissolved in water for injection to a concentration of 5 mg/ml. The solution is then poured into 10 ml vials which are then sealed.

EXAMPLE 6

Sterile (HH109) powder (50 mg) is aseptically packaged in 10 ml vials sealed with a rubber-stopper. Ten ml sterile water for injection is added to the vials in order to produce a 0.5 percent($5$ mg/ml) solution of (HH109).

EXAMPLE 7

The compounds HH109, GG195, KK100, LL46 were each separately dissolved 0.9 percent saline at a concentration of 2 mg/ml. Rhesus monkeys are anesthetized with halothane, nitrous oxide and oxygen. The maintenance concentration of halothane was 1.0%. Arterial and venous catheters were placed in the femoral vessels for drug administration and recording of the arterial pressure. Controlled ventilation was accomplished via an endotrachael tube. Twitch and tetanic contractions of the tibialis arterior muscle were elicited indirectly via the sciatic nerve. Recordings of arterial pressure electrocardiogram (lead I), heart rate, and muscle function were made simultaneously.

As shown in Table 1, four to six animals received each listed compound. Four additional animals received succinylcholine chloride or d-tubocurarine chloride as controls. The chart shows the dose range required to produce 95 percent block of the twitch response of the tibialis anterior muscle under above anesthetic conditions in each series of animals receiving each drug. Also listed in the chart is the range of the duration of action of each compound in each series of animals. Duration of action is defined as the time span from drug injection to full recovery of the twitch response of the tibialis anterior muscle.

The duration of action of these compounds in monkeys is more indicative of the possible duration of action of the compounds in man than studies done in other species, such as the cat and dog, for the following reason: the compounds are believed to be broken down (hydrolyzed) by an enyzeme (plasma cholinesterase) present in man, monkey, cat and dog. The rate of breakdown of any compound by this enzyme is believed to be the principal determinant of its duration of action in the body. The plasma cholinesterase activity of the rhesus monkey is known to be most similar to that of man (e.g., Hobbiger and Peck, British Journal of Pharmacology 37: 258–271, 1969).

TABLE 1

NEUROMUSCULAR BLOCKING POTENCY OF SELECTED COMPOUNDS IN THE RHESUS MONKEY

| COMPOUND | NUMBER OF ANIMALS TESTED | ED$_{95}$* (MG/NG CATION) | RANGE OF DURATION OF ACTION (MINUTES FROM INJECTION TO FULL RECOVERY) |
|---|---|---|---|
| HH109 | 4 | 0.1–0.4 | 20–30 |
| GG195 | 4 | 0.2–0.6 | 15–30 |
| KK100 | 4 | 1.0–3.0 | 10–20 |
| LL46 | 4 | 0.6–2.0 | 15–25 |
| Succinylcholine | 4 | 1.0–2.0 | 4–6 |
| 1-Tubecurarine | 4 | 0.2–0.4 | 30–50 |

*ED$_{95}$ means the dose necessary to produce 95 percent block of the twitch response of the tibialis anterior muscle stimulated indirectly at 0.15 Hz via the sciatic nerve.

EXAMPLE 8

Bis-3-[N-methyl-1-(3,4,5-trimethoxy benzyl)6,7-dimethoxy-1,2,3,4-tetrahydroisoquinolinium]propyl p-phenylene-3,3′-diacrylate dimesylate is prepared in an ion exchange reaction by reacting HH109 with silver mesylate. The dichloride HH109 is dissolved in water as is the silver mesylate. The reaction mixture is stirred to form the silver chloride precipitate. The mixture is filtered through filter paper to remove the silver chloride thereby leaving the mesylate salt in solution. The water is then evaporated.

EXAMPLE 9

Bis-3-[N-methyl-1-(3,4,5-trimethoxy benzyl)6,7-dimethoxy-1,2,3,4-tetrahydroisoquinolinium] propyl p-phenylene-3,3'-diacrylate ditosylate is prepared in an ion exchange reaction by reating HH109 with silver tosylate. The dichloride HH109 is dissolved in water as is the silver tosylate. The reaction mixture is stirred to form the silver chloride precipitate. The mixture is filtered through filter paper to remove the silver chloride thereby leaving the tosylate salt in soltuion. The water is then evaporated.

EXAMPLE 10

Preparation of Bis-3-[N-methyl-1-(3,4,5-trimethoxybenzyl)6, 7, dimethoxy-1,2,3,4-tetrahydroisoquinolinium]propyl m-phenylene-3,3'-diacrylate dichloride (LL39).

1. Preparation of silver m-phenylene diacrylate

| | |
|---|---|
| m-phenylene diacrylic acid 4.4 gm = | 40 meq |
| $H_2O$ | 60 ml |
| KOH 1N | 40 ml |

The mixture is heated to boiling, and, if necessary, the pH is adjusted to 7.0 with the same acid. $AgNO_3$ 6.8 gm = 40 m M is added to the yellow hot solution. Immediately a heavy precipitate forms. The mixture is cooled and filtered and the filter cake is washed with water, refiltered and dried. Yield = quantitative. The product is an amorphous, slightly colored powder. It is pulverized for use in the next step.

2. Preparation of 5'-Methoxylaudanosine

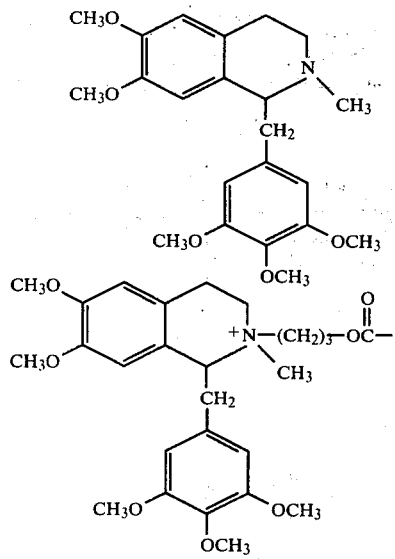

3,4-dimethoxyphenylethylamine and 3,4,5-trimethoxyphenylacetic acid are heated together at 165°–190° in a flask until bubbling of water subsides. The product, N-(3,4,5-trimethoxyphenyl acetyl)homoveratrylamine, is recrystallized from methanol. Yield = 80%. m.p. = 94°.

3.9 gm (10 mM) N-(3,4,5-trimethoxyphenylacetyl)-homoveratrylamine is refluxed in 15 ml toluene together with 5 ml $POCl_3$ for 2 hours. The settled semisolids are carefully separated ($POCl_3$ excess!) and the free base libertated by adding excess of NaOH and extracted with benzene. The product, 6,7-dimethoxy-1-(3',4',5'-trimethoxybenzyl) 3,4-dihydroisoquinoline is refluxed in acetone or benzene with an excess of methyl iodide. The quaternary salt, 6,7-dimethoxyl-(3',4',5'-trimethoxybenzyl)2-methyl 3,4-dihydroisoquinolinium iodide, precipitates out. m.p. = 224°.

5.1 gm (10 mM) 6,7-dimethoxy-1-(3',4',5'-trimethoxybenzyl)2-methyl 3,4-dihydroisoquinolinium iodide is dissolved in 80 ml $H_2O$ and 16 ml concentrated HCl. Zinc dust (1.1 gm) is added in small portions to the boiling stirred solution. The yellow color disappears (reaction time 15–20 minutes). The mixture is filtered hot from some unreacted zinc and rendered alkaline with concentrated NaOH. It is impractical to filter the partly precipitated zinc hydroxide, so to avoid emulsions, the whole mixture is carefully shaken with chloroform. The residue of the chloroform solution is redissolved in ether and the ether insolubles are filtered off. The ether residue does not crystallize on standing. This amine is a gummy material which hardens on standing. The crude amine is used in the next step.

3. Preparation of N-(3-chloropropyl)5'-methoxylaudanosinium bromide

5'-Methoxylaudanosine 1.4 gm = 4 mM is dissolved in 8 ml dimethylformamide by warming slightly. 1-bromo-3-chloropropane 1.2 gm (about 100% excess) is added and the mixture is left at room temperature for 5 days. (Sometimes part of the unreacted 5'-methoxylaudanosine crystallizes out, but eventually it redissolves).

The reddish-orange solution is treated with a large amount of ether and the precipitated gummy quaternary salt is decanted and slurried in fresh ether. After standing in ether for one day, low melting solids are obtained. Yield = 1.6 gm, about 80% of theory.

4. Preparation of m-phenylene diacrylic diester of N-propyl 5'-methoxylaudanosine (LL39) (Horenstein—Pahlicke Ester Formation)

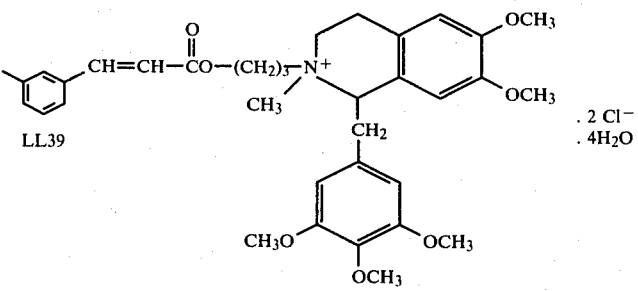

LL39

N-(3-chloropropyl)5'-methoxylaudanosinium bromide 2.1 gm = 4 mM
Silver m-phenylene diacrylate 0.85 gm = 4meg
$H_2O$ about 150 ml The mixture is boiled in an open beaker for about 10–15 minutes, stirring by hand from time to time. At the boiling temperature the silver salt is slightly soluble and reacts with the quaternary bromide. The mixture is cooled to room temperature, filtered straight and the aqueous solution is evaporated to dryness in a large dish on a steam bath. Continued heating of the residue is done for about 2 hours on a steam bath (90° C.), after which rearrangement to the ester is complete:

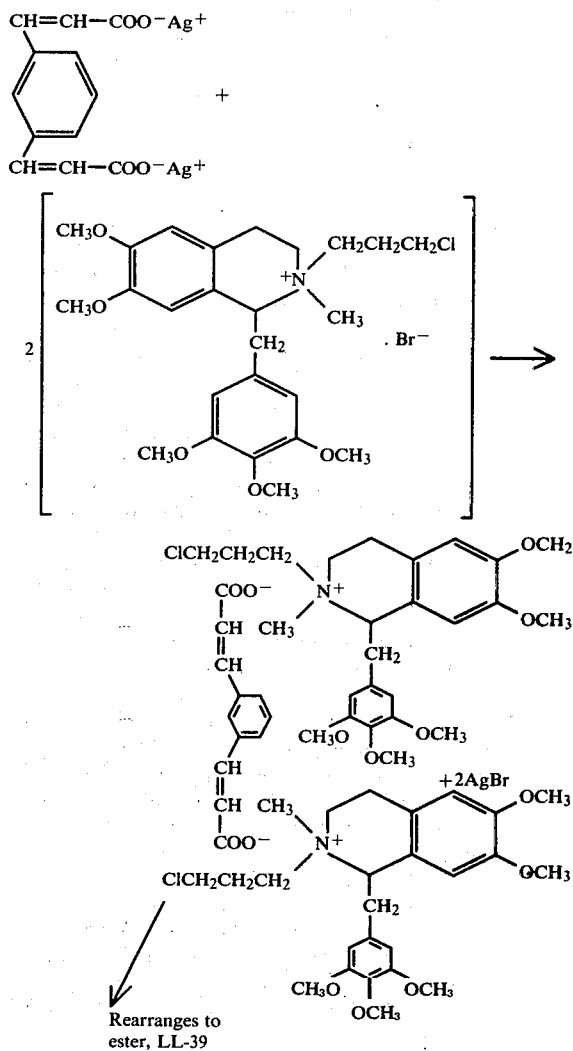

Rearranges to ester, LL-39

The amorphous residue is boiled with isopropanol (about 40 ml) and filtered hot from some trace mechanical impurities. Gums precipitate from the filtrate at room temperature and the precipitation is completed at about −3° overnight. The supernatant is decanted and the material is slurried in ethyl acetate twice. By now the gum is semisolid and can be filtered off. After careful drying at 75° the gums become solids. At this stage they still probably retain water in varying degrees. Yield=1.0 gm (about 40%) Yields vary from batch to batch. A pharmaceutical formulation of LL39 is prepared as in Example 5 or 6.

EXAMPLE 11

The compound of EXAMPLE 10 (LL-39) is converted to the dimesylate salt in an ion exchange reaction by reacting LL39 with silver mesylate. The dichloride (LL39) is dissolved in water as is the silver mesylate. The reaction mixture is stirred to form the silver chloride precipitate. The mixture is then filtered through filter paper to remove the silver chloride leaving the mesylate salt. Bis-3-[N-methyl-1-(3,4,5-trimethoxybenzyl)6,7-dimethoxy-1,2,3,4-tetrahydroisoquinolinium] propyl m-phenylene-3,3'diacrylate dimesylate in solution. The water is then evaporated.

EXAMPLE 12

The compound of EXAMPLE 10 (LL-39) is converted to the ditosylate salt in an ion exchange reaction by reacting LL39 with silver tosylate. The dichloride (LL39) is dissolved in water as is the silver tosylate. The reaction mixture is stirred to form the silver chloride precipitate. The mixture is then filtered through filter paper to remove the silver chloride leaving the tosylate salt. Bis-3-[N-methyl-1-(3,4,5-trimethoxybenzyl)6,7-dimethoxy-1,2,3,4-tetrahydroisoquinolinium]propyl m-phenylene-3,3'diacrylate ditosylate in solution. The water is then evaporated.

EXAMPLE 13

Following the procedures of the above examples, the following compounds as dichlorides have been made.

| NO | R | B, C RELATIONSHIP | W | Y | Z | $R_1$ | $R_2$ | $R_3$ | $R_4$ |
|---|---|---|---|---|---|---|---|---|---|
| GG32 | 3 | para | CH=CH | $CH_3$ | H | H | $OCH_3$ | $OCH_3$ | H |
| GG45 | 3 | para | " | " | $CH_3$ | " | " | " | " |
| GG46 | 2 | para | " | " | " | " | " | " | " |
| GG122 | 3 | meta | " | " | " | " | " | " | " |
| GG179 | 2 | para | " | " | " | $OCH_3$ | " | " | " |
| HH79 | 3 | para | " | " | " | " | " | " | " |
| MM168 | 3 | para | " | " | " | H | " | " | $OCH_3$ |
| KK186 | 3 | meta | " | " | 3,4-dimethoxybenzyl ,5- | H | " | " | H |
| LL39 | 3 | meta | " | " | 3,4/trimethoxybenzyl | H | " | " | H |
| NN106 | 3 | meta | $CH_2$ | " | 3,4-dimethoxybenzyl ,5- | H | " | " | H |
| OO155 | 3 | meta | $CH_2$ | " | 3,4/trimethoxybenzyl | H | " | " | H |

We claim:
1. A compound of the formula

[Structure: bis-tetrahydroisoquinolinium compound with fumarate-type linker, .2X⁻]

where X is a pharmaceutically acceptable anion.

2. The compound of claim 1 in which the X is iodide, mesylate, tosylate, bromide, chloride, sulfate, phosphate, hydrogen phosphate, acetate or propionate.

3. The compound of claim 1 in which X is chloride.

4. The compound of claim 1 in which X is mesylate.

5. The compound of claim 1 in which X is tosylate.

6. A method of producing muscle relaxation in mammal which comprises parenterally administering to said mammal an effective neuromuscular blocking amount of the compound of claim 1, 2, 3, 4, or 5.

7. The method of claim 6 in which the mammal is a human.

8. The method of claim 6 in which the compound is administered intraveniously.

9. The method of claim 7 in which the compound is administered intraveniously.

10. A pharmaceutical formulation for use as a muscle relaxant comprising the compound of any one of claims 1, 2, 3, 4, or 5, and a pharmaceutically acceptable carrier therefore.

11. A pharmaceutical formulation of claim 10 in which the amount of the compound is 5 to 400 mg.

12. A compound of the formula

[Structure diagram]

where X is a pharmaceutically acceptable anion.

13. The compound of claim 12 in which the X is iodide, mesylate, tosylate, bromide, chloride, sulfate, phasphate, hydrogen phosphate, acetate or propionate.

14. The compound of claim 12 in which X is chloride.

15. The compound of claim 12 in which X is mesylate.

16. The compound of claim 12 in which X is tosylate.

17. A method of producing muscle relaxation in a mammal which comprises parenterally administering to said mammal an effective neuromuscular blocking amount of the compound of claim 12, 13, 14, 15 or 16.

18. The method of claim 17 in which the mammal is a human.

19. The method of claim 17 in which the compound is administered intraveniously.

20. The method of claim 17 in which the compound is administered intravenously.

21. A pharmaceutical formulation for use as a muscle relaxant comprising the compound of anyone of claims 12, 13, 14, 15 or 16 and a pharmaceutically acceptable carrier therefore.

22. A pharmaceutical formulation of claim 21 in which the amount of the compound is 5 to 400 mg.

23. A compound of the formula (I)

$$B\text{—}\phantom{X}\text{—}C \cdot 2X^-$$ (I)

where B and C are para or meta and are each

[Structure showing —W—C(=O)—O—(CH₂)ₙ—N⁺ with tetrahydroisoquinoline having R₁, R₂, R₃, R₄ substituents, Y and Z]

where W is CH=CH $R_1$, $R_2$, $R_3$ and $R_4$ are the same or different and are each hydrogen or lower alkoxy of 1 to 4 carbon atoms Y is lower alkyl of 1 to 4 carbons Z is hydrogen, lower alkyl of 1 to 4 carbon atoms, cyclopentyl, cyclohexyl, benzyl, or

[Structure: —CH₂—phenyl with O—ALKYL, O—ALKYL or H, O—ALKYL or H substituents]

where ALKYL has 1 to 4 carbon atoms, n is 2, 3 or 4, provided that at least one of $R_1$ to $R_4$ is lower alkoxy and X is a pharmaceutically acceptable anion.

24. The compound of claim 23 in which Y is methyl.

25. The compound of claim 23 in which $R_1$ and $R_4$ are hydrogen and $R_2$ and $R_3$ are methoxy.

26. The compound of claim 23 in which $R_1$ and $R_4$ are hydrogen, $R_2$ and $R_3$ are methoxy and n is 3.

27. The compound of claim 23 in which Z is benzyl substituted at the 3, 4, or 3, 4, 5, position of the phenyl ring with methoxy, $R_1$ and $R_4$ are hydrogen, $R_2$ and $R_3$ are methoxy and n is 3.

28. The compound of claim 23 in which B is para to C.

29. The compound of claim 23 in which B is meta to C.

30. The compound of claim 27 in which B is para to C.

31. The compound of claim 27 in which B is meta to C.

32. The compound of claim 28 in which n is 3, Y is $CH_3$, Z is hydrogen, $R_1$ and $R_4$ are hydrogen and $R_2$ and $R_3$ are methoxy.

33. The compound of claim 28 in which n is 3, Y is $CH_3$, Z is $CH_3$, $R_1$ and $R_4$ are hydrogen and $R_2$ and $R_3$ are methoxy.

34. The compound of claim 28 or 29 in which n is 3, Y is $CH_3$, Z is 3, 4-dimethoxybenzyl, $R_1$ and $R_4$ are hydrogen and $R_2$ and $R_3$ are methoxy.

35. The compound of claim 28 or 29 in which n is 3, Y is $CH_3$, Z is 3,4,5-trimethoxybenzyl, $R_1$ and $R_4$ are H and $R_2$ and $R_3$ are methoxy.

36. The compound of claim 24 in which $R_1$ and $R_4$ are hydrogen and $R_2$ and $R_3$ are methoxy.

37. The compound of claim 24 in which $R_1$ and $R_4$ are hydrogen, $R_2$ and $R_3$ are methoxy and n is 3.

38. The compound of claim 24 in which Z is benzyl substituted at the 3, 4, or 3, 4, 5, position of the phenyl ring with methoxy, $R_1$ and $R_4$ are hydrogen, $R_2$ and $R_3$ are methoxy and n is 3.

39. The compound of claim 29 in which n is 3, Y is $CH_3$, Z is hydrogen, $R_1$ and $R_4$ are hydrogen and $R_2$ and $R_3$ are methoxy.

40. The compound of claim 29 in which n is 3, Y is $CH_3$, Z is $CH_3$, $R_1$ and $R_4$ are hydrogen, and $R_2$ and $R_3$ are methoxy.

41. The compound of claims 24, 25, 26, 27, 28, 29, 30, 31, 32, 33, 36, 37, 38 or 40, in which the anion is phosphate, acetate or propionate.

42. The compound of claim 34 in which X is chloride.

43. The compound of claim 28 in which n is 2, Y is $CH_3$, Z is $CH_3$, $R_1$, $R_2$ and $R_3$ are methoxy, and $R_4$ is hydrogen.

44. The compound of claim 28 in which n is 3, Y is $CH_3$, Z is $CH_3$, $R_1$, $R_2$, and $R_3$ are methoxy and $R_4$ is hydrogen.

45. The compound of claim 28 in which n is 3, Y is $CH_3$, Z is $CH_3$, $R_1$ is hydrogen, and $R_2$, $R_3$, and $R_4$ are methoxy.

46. The compound of claim 29 in which n is 3, Y is $CH_3$, Z is 3,4 dimethoxybenzyl, $R_1$ and $R_4$ are hydrogen, and $R_2$ and $R_3$ are methoxy.

47. The compound of claims 43, 44, 45 or 46 in which X is chloride.

48. A compound of the formula

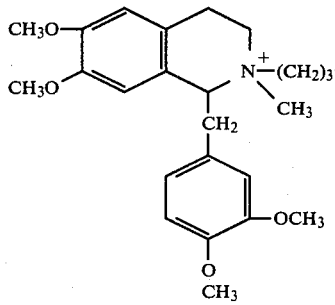

where X is a pharmaceutically acceptable anion.

49. The compound of claim 48 in which the X is iodide, mesylate, tosylate, bromide, chloride, sulfate, phosphate, hydrogen phosphate, acetate or propionate.

50. The compound of claim 48 in which X is chloride.

51. The compound of claim 48 in which X is mesylate.

52. The compound of claim 48 in which X is tosylate.

53. The compound of claim 34 in which the anion is iodide, mesylate, tosylate, bromide, chloride, sulfate, phosphate, hydrogen phosphate, acetate or propionate.

54. The compound of claim 35 in which the anion is iodide, mesylate, tosylate, bromide, chloride, sulfate, phosphate, hydrogen phosphate, acetate or propionate.

55. A method of producing muscle relaxation in a mammal which comprises parenterally administering to said compound of claim 23, 24, 25, 26, 27, 28, 29, 30, 31, 32, 33, or 40.

56. The method of claim 45 in which the compound is administered intravenously.

57. The method of claim 55 in which the mammal is a human.

58. A pharmaceutical preparation for use as a muscle relaxant comprising the compound of anyone of claims 23, 24, 25, 26, 27, 28, 29, 30, 31, 32, 33, 34, 35, 36, 37, 38, 39 or 40, and a pharmaceutically acceptable carrier therefore.

59. The preparation according to claim 34 in which the compound is present in an amount effective as an effective neuromuscular blocking agent.

60. The preparation according to claim 59 in which the amount is 5 to 400 mg.

61. The method of claim 56 in which the mammal is a human.

62. The preparation according to claim 10 in which the compound is present in a amount effective as an effective neuromuscular blocking agent.

63. The preparation according to claim 21 in which the compound is present in a amount effective as an effective neuromuscular blocking agent.

64. A method of producing muscle relaxation in a mammal which comprises parenterally administering to said mammal an effective neuromuscular blocking amount of the compound of claim 42.

65. A pharmaceutical preparation for use as a muscle relaxant comprising the compound of claim 42, and a pharmaceutically acceptable carrier therefore.

66. A method of producing muscle relaxation in a mammal which comprises parenterally administering to said mammal an effective neuromuscular blocking amount of the compound of claim 47.

67. A pharmaceutical preparation for use as a muscle relaxant comprising the compound of claim 47, and a pharmaceutically acceptable carrier therefore.

68. A method of producing muscle relaxation in a mammal which comprises parenterally administering to said mammal an effective neuromuscular blocking amount of the compound of claims 48, 49, 50, 51, or 52.

69. The method of claim 68 in which the mammal is a human.

70. The method of claim 69 in which the compound is administered intravenously.

71. The method of claim 70 in which the compound is administered intravenously.

72. A pharmaceutical formulation for use as a muscle relaxant comprising the compound of claims 48, 49, 50, 51, or 52, and a pharmaceutically acceptable carrier therefore.

73. A pharmaceutical formulation of claim 72 in which the amount of the compound is 5 to 400 mg.

74. A method of producing muscle relaxation in a mammal which comprises parenterally administering to said mammal an effective neuromuscular blocking amount of the compound of claim 34.

75. The method of claim 74 in which the compound is administered intravenously.

76. The method of claims 74 or 75 in which the mammal is a human.

77. A pharmaceutical preparation for use as a muscle relaxant comprising the compound of claim 34 and a pharmaceutically acceptable carrier therefore.

78. The preparation according to claim 77 in which the compound is present in an amount effective as an effective neuromuscular blocking agent.

79. The preparation according to claim 78 in which the amount is 5 to 400 mg.

80. The preparation according to claim 78 in which the amount is 5 to 200 mg.

81. The preparation according to claim 78 in which the amount is 1 to 100 mg.

82. The preparation according to claim 78 in which the amount is 3 to 50 mg.

83. A method of producing muscle relaxation in a mammal which comprises parenterally administering to said mammal an effective neuromuscular blocking amount of the compound of claim 35.

84. The method of claim 83 in which the compound is administered intravenously.

85. The method of claims 83 or 84 in which the mammal is a human.

86. A pharmaceutical preparation for use as a muscle relaxant comprising the compound of claim 35 and a pharmaceutically acceptable carrier therefore.

87. The preparation according to claim 86 in which the compound is present in an amount effective as an effective neuromuscular blocking agent.

88. The preparation according to claim 87 in which the amount is 5 to 400 mg.

89. The preparation according to claim 88 in which the amount is 5 to 200 mg.

90. The preparation according to claim 88 in which the amount is 1 to 100 mg.

91. The preparation according to claim 88 in which the amount is 3 to 50 mg.

92. The preparation according to claim 72 in which the amount is 5 to 200 mg.

93. The preparation according to claim 72 in which the amount is 1 to 100 mg.

94. The preparation according to claim 72 in which the amount is 3 to 50 mg.

95. The preparation of claim 11 in which the amount is 5 to 2000 mg.

96. The preparation of claim 11 in which the amount is 1 to 100 mg.

97. The preparation of claim 11 in which the amount is 3 to 50 mg.

* * * * *